United States Patent
Fogel et al.

(10) Patent No.: US 12,329,704 B2
(45) Date of Patent: Jun. 17, 2025

(54) ABSORBENT REPOSITIONING PAD AND METHOD

(71) Applicant: Medline Industries, LP, Northfield, IL (US)

(72) Inventors: Jeremy Fogel, Evanston, IL (US); Rachel Sinde, Des Plaines, IL (US)

(73) Assignee: Medline Industries, LP, Northfield, IL (US)

( * ) Notice: Subject to any disclaimer, the term of this patent is extended or adjusted under 35 U.S.C. 154(b) by 789 days.

(21) Appl. No.: 17/409,684

(22) Filed: Aug. 23, 2021

(65) Prior Publication Data
US 2023/0064553 A1    Mar. 2, 2023

(51) Int. Cl.
| A61G 7/10 | (2006.01) |
| A61F 13/15 | (2006.01) |
| A61F 13/513 | (2006.01) |
| A61F 13/514 | (2006.01) |

(52) U.S. Cl.
CPC ...... *A61G 7/1026* (2013.01); *A61F 13/15203* (2013.01); *A61F 13/513* (2013.01); *A61F 13/51456* (2013.01); *A61F 2013/15154* (2013.01); *A61F 2013/15276* (2013.01); *A61F 2013/15406* (2013.01); *A61G 2200/322* (2013.01); *A61G 2200/327* (2013.01)

(58) Field of Classification Search
CPC .. A61G 7/10; A61G 7/1026; A61G 2200/322; A61G 2200/327; A61F 13/15203; A61F 13/513; A61F 13/51456; A61F 2013/15154; A61F 2013/15276; A61F 2013/15406
See application file for complete search history.

(56) References Cited

U.S. PATENT DOCUMENTS

| 4,704,114 A | 11/1987 | Wilson |
| 5,411,498 A | 5/1995 | Fahrenkrug |
| 5,496,298 A | 3/1996 | Kuepper |
| 5,527,302 A | 6/1996 | Endres |
| 5,607,760 A | 3/1997 | Roe |
| 5,638,558 A | 6/1997 | Moore |
| 5,693,411 A | 12/1997 | Hansen |
| 5,787,523 A | 8/1998 | Lindberg |
| 5,817,325 A | 10/1998 | Sawan |

(Continued)

FOREIGN PATENT DOCUMENTS

WO    2015106239    7/2015

OTHER PUBLICATIONS

Medline Industries, Inc., PerforMAX LT Reusable Underpads Brochure, 2014.

(Continued)

*Primary Examiner* — Fredrick C Conley
(74) *Attorney, Agent, or Firm* — Fitch, Even, Tabin & Flannery LLP

(57) ABSTRACT

An absorbent repositioning pad includes an upper layer including a liquid permeable material, and a lower layer having relatively lower friction surface than the upper layer. The absorbent repositioning pad further includes a first intermediate layer between the upper and lower layers and including an absorbent material, and a second intermediate layer between the first intermediate layer and the lower layer and including a liquid impermeable material.

15 Claims, 7 Drawing Sheets

(56) References Cited

U.S. PATENT DOCUMENTS

| | | |
|---|---|---|
| 5,843,056 A | 12/1998 | Good |
| 5,873,870 A | 2/1999 | Seitz |
| 5,957,908 A | 9/1999 | Kline |
| 5,993,840 A | 11/1999 | Fawkes |
| 6,086,571 A | 7/2000 | Guevara |
| 6,149,934 A | 11/2000 | Krzysik |
| 6,153,209 A | 11/2000 | Vega |
| 6,180,584 B1 | 1/2001 | Sawan |
| 6,217,890 B1 | 4/2001 | Paul |
| 6,233,762 B1 | 5/2001 | Bradley |
| 6,287,581 B1 | 9/2001 | Krzysik |
| 6,296,862 B1 | 10/2001 | Paul |
| 6,316,013 B1 | 11/2001 | Paul |
| 6,436,418 B1 | 8/2002 | Sheldon |
| 6,475,197 B1 | 11/2002 | Krzysik |
| 6,482,422 B1 | 11/2002 | Paul |
| 6,494,871 B1 * | 12/2002 | Lariviere .......... A61F 13/53713 604/385.01 |
| 6,503,525 B1 | 1/2003 | Paul |
| 6,503,526 B1 | 1/2003 | Krzysik |
| 6,515,029 B1 | 2/2003 | Krzysik |
| 6,534,074 B2 | 3/2003 | Krzysik |
| 6,570,054 B1 | 5/2003 | Gatto |
| 6,586,652 B1 | 7/2003 | Roe |
| 6,651,278 B2 | 11/2003 | Ghanem |
| 6,689,932 B2 | 2/2004 | Kruchoski |
| 6,703,536 B2 | 3/2004 | Roe |
| 6,706,941 B2 | 3/2004 | Hisanaka |
| 6,728,978 B1 * | 5/2004 | Nordin ................. A47C 27/005 5/81.1 HS |
| 6,732,389 B2 | 5/2004 | Drexler |
| 6,749,860 B2 | 6/2004 | Tyrrell |
| 6,756,520 B1 | 6/2004 | Krzysik |
| 6,800,789 B2 | 10/2004 | Kasai |
| 6,834,402 B2 | 12/2004 | Hanson |
| 6,835,865 B2 | 12/2004 | Quincy, III |
| 6,855,134 B2 | 2/2005 | Brooks |
| 6,867,287 B2 | 3/2005 | Carlucci |
| 6,887,564 B2 | 5/2005 | Gagliardini |
| 6,960,702 B1 | 11/2005 | Kawakami |
| 6,967,025 B2 | 11/2005 | Di Cintio |
| 7,060,867 B2 | 6/2006 | Jameson |
| 7,103,929 B2 | 9/2006 | Pilling |
| 7,120,952 B1 | 10/2006 | Bass |
| 7,265,257 B2 | 9/2007 | Baldwin |
| 7,287,650 B2 | 10/2007 | Koslow |
| 7,345,215 B2 | 3/2008 | Fernfors |
| 7,655,828 B2 | 2/2010 | Rajagopalan |
| 7,836,528 B2 | 11/2010 | Nuckton |
| 7,849,532 B1 | 12/2010 | Servais |
| 8,011,041 B2 | 9/2011 | Hann |
| 8,701,225 B1 | 4/2014 | Latiff |
| 8,789,533 B2 | 7/2014 | Steffens |
| 8,791,321 B2 | 7/2014 | Love |
| 8,850,634 B2 | 10/2014 | Ponsi |
| 8,984,681 B2 | 3/2015 | Ponsi |
| 9,241,853 B2 | 1/2016 | Carlson |
| 9,414,977 B2 | 8/2016 | Ponsi |
| 9,533,479 B2 | 1/2017 | Yao |
| 9,717,818 B2 | 8/2017 | Yao |
| 9,724,256 B2 | 8/2017 | Love |
| 9,795,529 B2 | 10/2017 | Lehtio |
| 9,808,387 B2 | 11/2017 | Love |
| 9,820,905 B2 * | 11/2017 | Bullock .................. A61G 1/01 |
| 10,154,741 B2 | 12/2018 | Duck |
| 10,211,349 B2 | 2/2019 | Harley |
| 10,314,417 B2 | 6/2019 | Duck |
| 10,624,804 B2 | 4/2020 | Williams |
| 10,905,264 B1 | 2/2021 | Getschow |
| 2005/0222227 A1 | 10/2005 | Chen |
| 2006/0025731 A1 | 2/2006 | Cohen |
| 2006/0089413 A1 | 4/2006 | Schmaus |
| 2007/0054967 A1 | 3/2007 | Schmaus |
| 2007/0059331 A1 | 3/2007 | Schmaus |
| 2007/0077428 A1 | 4/2007 | Hamed |
| 2007/0142806 A1 | 6/2007 | Roe |
| 2007/0213412 A1 | 9/2007 | Bacon |
| 2007/0265590 A1 | 11/2007 | Sakaguchi |
| 2007/0298064 A1 | 12/2007 | Koslow |
| 2008/0095719 A1 | 4/2008 | Herrmann |
| 2008/0147027 A1 | 6/2008 | Sanabria |
| 2010/0047303 A1 | 2/2010 | Yhlen |
| 2011/0119831 A1 * | 5/2011 | Rincon .................... A61G 1/01 5/627 |
| 2012/0053545 A1 * | 3/2012 | Love ......................... B32B 7/14 604/374 |
| 2012/0186013 A1 * | 7/2012 | Ponsi ..................... A61G 7/001 5/81.1 R |
| 2013/0152950 A1 | 6/2013 | Giap |
| 2013/0270881 A1 * | 10/2013 | Fowler ..................... A61G 5/10 297/219.1 |
| 2014/0123384 A1 | 5/2014 | White |
| 2014/0304918 A1 * | 10/2014 | Steffens ............... A61G 7/1025 5/617 |
| 2015/0216751 A1 | 8/2015 | Stokes |
| 2017/0296414 A1 | 10/2017 | Fowler |
| 2018/0256412 A1 | 9/2018 | Love |

OTHER PUBLICATIONS

International Search Report and Written Opinion for Application PCT/US2022/037844 mailed Nov. 11, 2022.

* cited by examiner

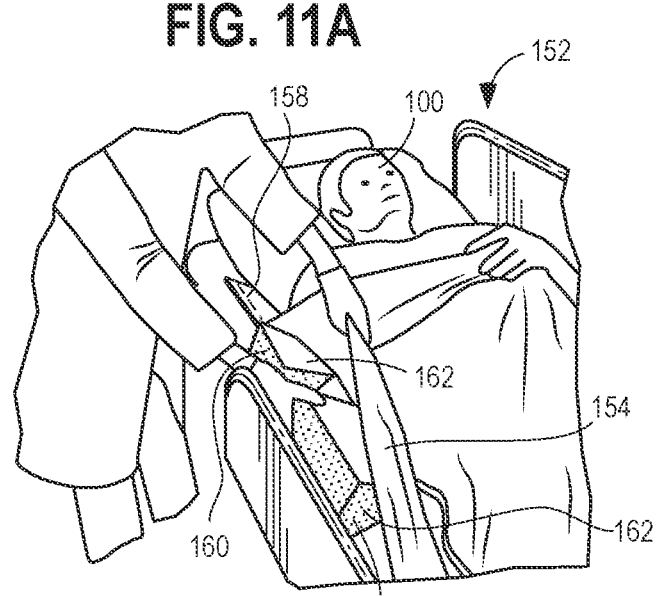
FIG. 11A
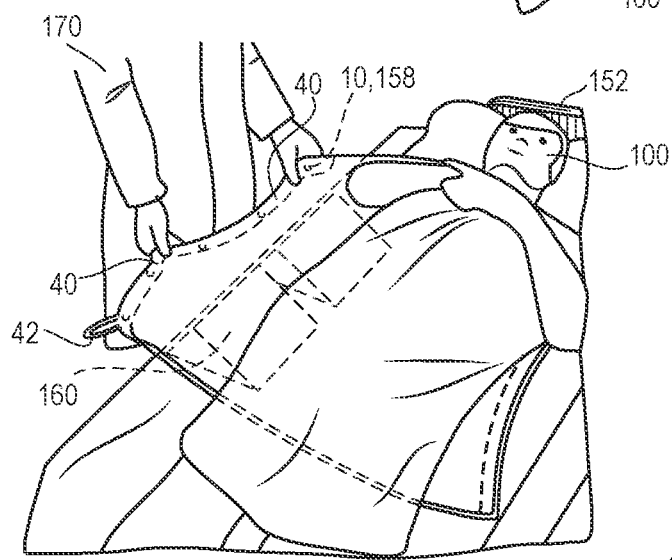
FIG. 11B
FIG. 11C
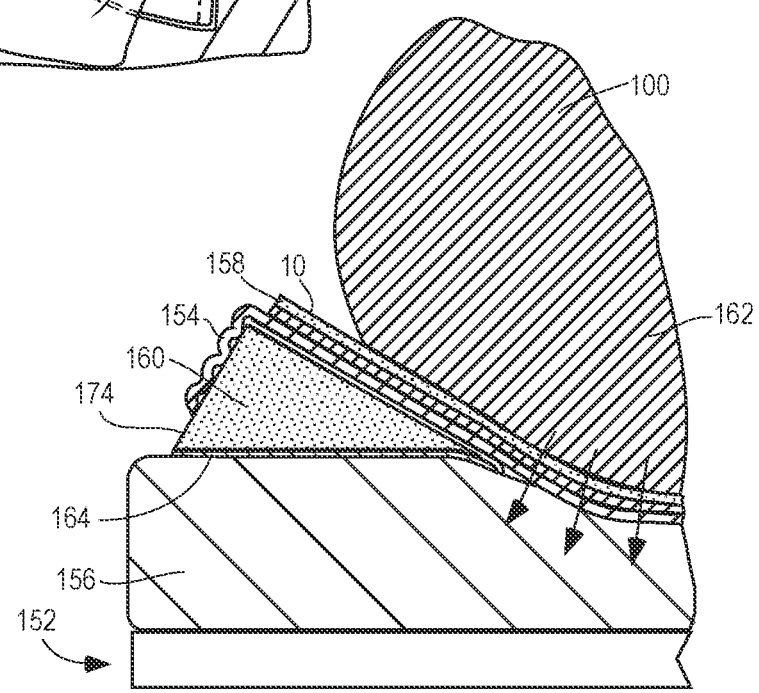

ABSORBENT REPOSITIONING PAD AND METHOD

TECHNICAL FIELD

This disclosure relates to repositioning sheets and more particularly, to absorbent and reusable repositioning sheets.

BACKGROUND

In hospitals, nursing homes, and other healthcare facilities, it is necessary to address patient incontinence. Absorbent articles such as incontinent briefs, diapers, and underpads can address incontinence by absorbing and containing liquid and other discharges from the human body. Typical absorbent underpads include a topsheet facing the wearer that permits liquid to pass through and a backsheet that prevents the liquid from escaping from the absorbent article.

Relatedly, individuals who are bed-ridden or otherwise immobilized may experience bed sores (also known as pressure ulcers or decubitus ulcers) that may be caused by pressure exerted on their skin and soft tissue. Bed sores may be exacerbated when the skin is exposed to moisture (e.g., due to incontinence). Bed sores may also be exacerbated by friction, heat, and shear forces caused, for example, by moving or repositioning a bed-ridden patient. To alleviate bedsores, bedridden patients need to be repositioned frequently. Patients also need to be transferred from one surface to another; for example, to change bed linens or to transfer the patient from a bed to a gurney for a medical procedure.

A patient repositioning device that functions to absorb liquids and that may be laundered is now provided, addressing each of the foregoing concerns. The device takes the form of an absorbent repositioning pad as described herein. In many cases the disclosed pad is launderable to permit reuse. Related methods for patient repositioning have also been devised as addressed below.

BRIEF DESCRIPTION OF THE DRAWINGS

FIG. 11A is a perspective view of a patient repositioning systems showing wedges being inserted below a patient positioned on an absorbent repositioning pad.

FIG. 11B is a perspective view of the patient and the absorbent repositioning pad being slid over and across the wedges for repositioning the patient.

FIG. 11C is a cross-sectional view showing the patient and the absorbent repositioning pad slid over the wedges.

DETAILED DESCRIPTION

The absorbent repositioning pads described herein absorb moisture to assist in maintaining skin dryness and preventing leakage of bodily fluids. The absorbent repositioning pads also may allow air circulation between the pad and the surface of the patient's skin to reduce heat buildup and maintain skin health. Furthermore, the absorbent repositioning pads described herein are sufficiently strong to allow the patient to be repositioned, for example to change bed linens, for medical procedures, or to prevent the formation of pressure ulcers, even when the pad is wet. Various uses for of the absorbent repositioning pads are described in U.S. Pat. No. 8,791,321, which is hereby incorporated by reference.

Figure 1:
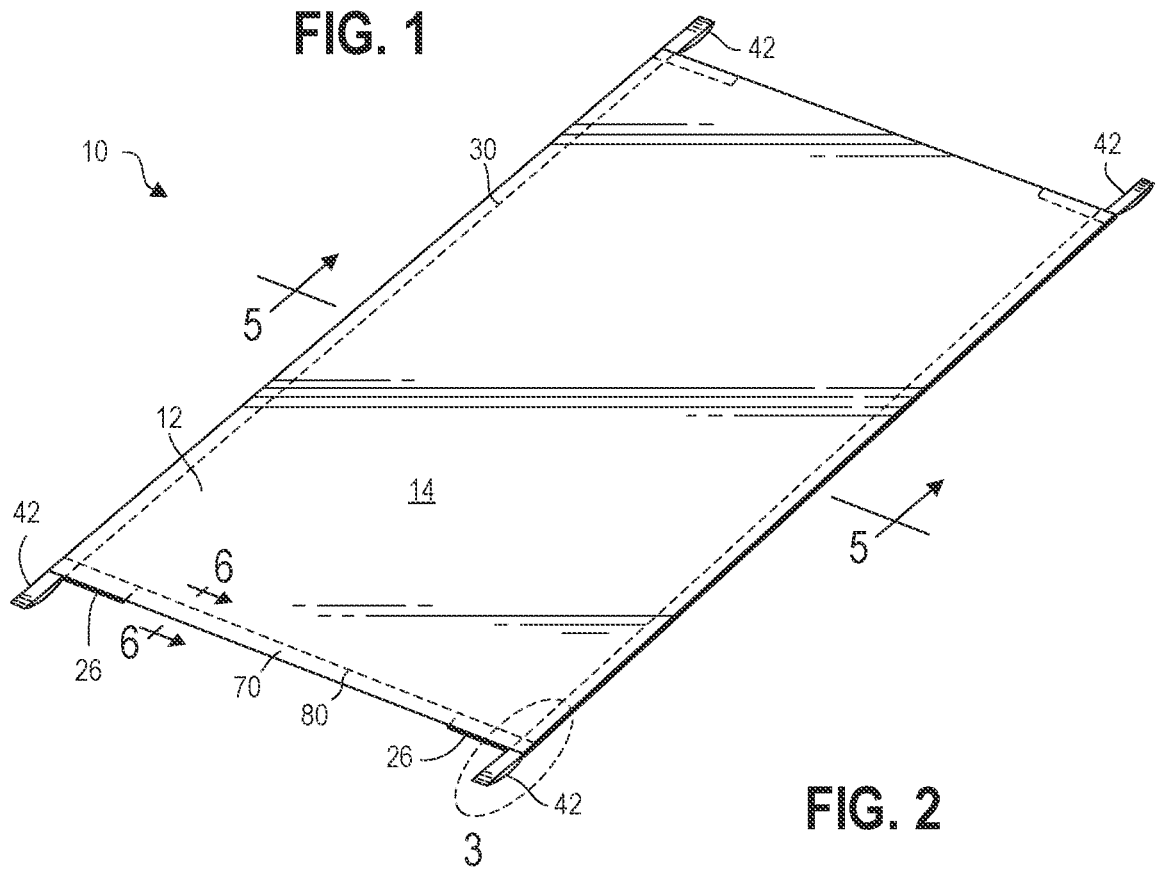
FIG. 1 is a top perspective view of an exemplary absorbent repositioning pad.
Figure 2:
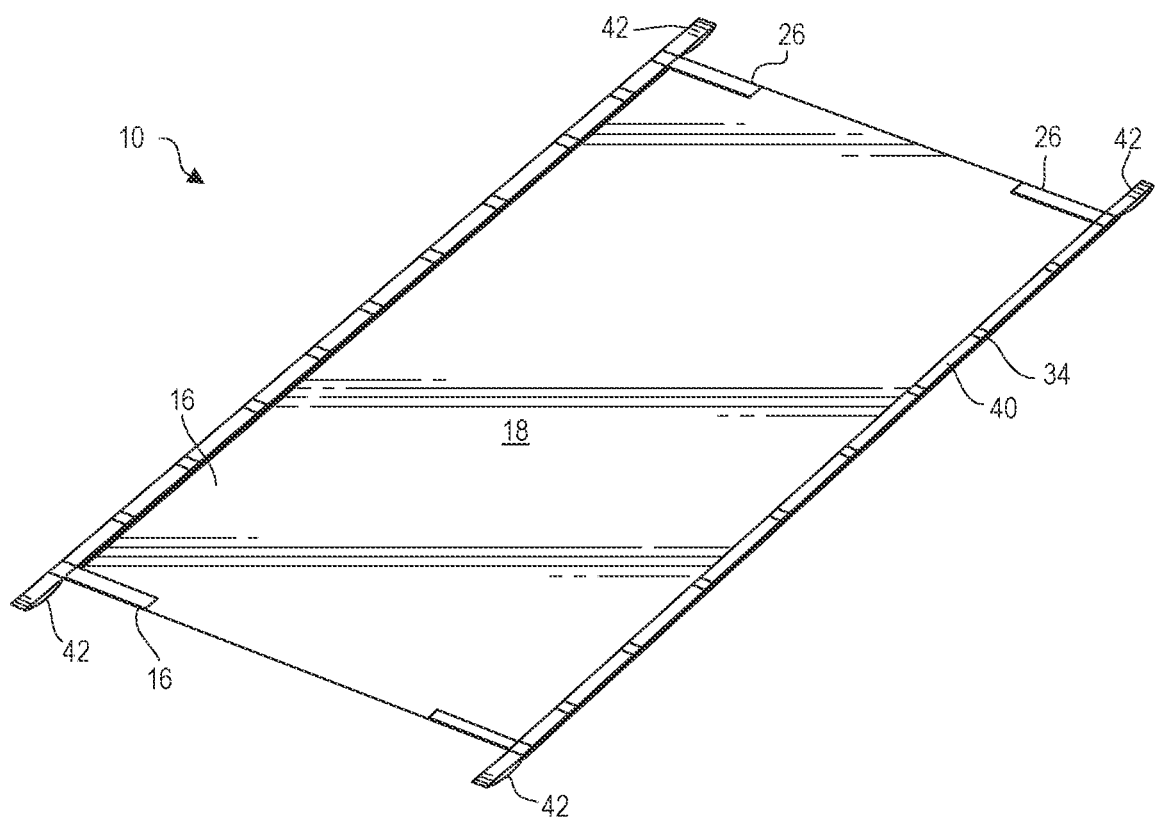
FIG. 2 is a bottom perspective view of the absorbent repositioning pad shown in FIG. 1.

Referring now to FIGS. 1 and 2, the exemplary absorbent repositioning pad 10 is a multilayer, absorbent, and reusable underpad that provides for both incontinence management and repositioning of a patient. The pad 10 includes an upper sheet or layer 12, shown in FIG. 1, that has an upper surface 14 upon which the patient may rest. The upper layer 12 includes a breathable, liquid permeable material. The upper layer 12 may be formed, for example, of a polymeric material such as a brushed, knit polyethylene terephthalate (PET). Other polymeric materials may include polypropylene, polyethylene, polyamide, viscose rayon, nylon, or the like or any combinations thereof. As used herein, a "brushed" surface refers to fabric that has undergone a brushing process that produces fine fibers from the knit yarns. The upper layer 12 may also or instead include a fiber material such as cotton. For example, the upper layer 12 may be a brushed cotton poly twill. The brushed upper surface 14 of the upper layer 12 is generally soft to the touch, and in some instances, may reduce sliding of a patient supported thereon relative to the pad 10.

The upper layer 12 may be hydrophilic. The upper layer 12 may also or instead be hydrophobic. If the layer is composed of plural materials then a portion may be hydrophilic and a portion hydrophobic.

The pad 10 further includes a lower sheet or layer 16, shown in FIG. 2, that has a lower surface 18 that contacts a patient support such as a bed or gurney. The lower layer 16 includes a breathable, liquid impermeable material. The lower layer 16 may be hydrophobic or hydrophilic. For example, the lower layer 16 may be formed of a fabric that includes filament synthetic yarns, such as extruded PET. The lower layer 16 should be constructed so as not to permit passage of urine therethrough during a period of intended use. Preferably, the lower layer 16 has a moisture vapor transmission rate (MTVR) in the range of about 1,000 g/m²/day to about 10,000 g/m²/day as measured by ASTM E95M-05. For example, the MTVR can be about 1,000 g/m²/day, about 2,000 g/m²/day, about 3,000 g/m²/day, about 4,000 g/m²/day, about 5,000 g/m²/day, about 6,000 g/m²/day, about 7,000 g/m²/day, about 8,000 g/m²/day, about 9,000 g/m²/day, about 10,000 g/m²/day, or greater than 10,000 g/m²/day, or in each case from that value up to 10,000 g/m²/day.

At least a portion of the lower layer 16 (e.g., lower surface 18) is a relatively lower friction surface than the upper layer 12. By this it is contemplated that, as compared to a brushed surface such as upper surface 14, the lower surface 18 of the pad 10 has a lower coefficient of friction when evaluated against a bedsheet (e.g., a cotton-polyester blend or polyester bedsheet). In this way, the lower layer 16 allows a caregiver to slide the pad 10 and patient supported thereon with greater ease. The lower surface 18 of the lower layer 16 may be a generally smooth surface that is not brushed. More particularly, the lower surface 18 may be formed of filament yarn is not brushed. The non-brushed filament yarn of the lower layer 16 provides a generally smooth lower surface 18 as compared to, for example, spun yarn, whether brushed or not brushed.

The fabric of the lower surface 18 may be formed of a woven fabric such that the fabric yarns are interlaced generally at right angles. As compared to a knit fabric, which includes yarns oriented in many different directions, the two-direction orientation of the fabric of the lower surface 18 has a lower coefficient of friction between the pad 10 and a cotton bedsheet, which is a typical surface on which the pad 10 is supported. The woven property of the fabric, in conjunction with the yarn being non-brushed filament yarn as discussed above, contributes to the lower layer 16 having a relatively lower friction lower surface 18 as compared to the upper surface 14 of the upper layer 12.

Table 1 below shows forces required to initiate movement and to maintain movement, as measured by ASTM D1894, of the lower surface 18 of three pads 10 as compared to two alternative pads. Pad A includes a lower surface 18 formed of nylon. Pad B includes a lower surface 18 formed of polyester. Pad C includes a lower surface 18 formed of acetate. The three pads 10A, B, and C and two comparison pads D and E were each tested against themselves, against a woven sheet, and against a knit sheet. Pad D is a Maximum Absorbency Premium Underpad sold by Cardinal Health, and Pad E is a SafetySure MovEase Underpad sold by MTS Medical Supply.

As demonstrated by the lower forces required to initiate movement and to maintain movement, the coefficients of friction of the three pads 10A, B, and C relative to one another (bottom surfaces of each pad), relative to the woven sheet, and relative to the knit sheet were less than those of the two comparison pads D and E.

TABLE 1

| | Test against self | | Test against woven sheet | | Test against knit sheet | |
|---|---|---|---|---|---|---|
| | Initiate (static) in lbf | Maintain (kinetic) in lbf | Initiate (static) in lbf | Maintain (kinetic) in lbf | Initiate (static) in lbf | Maintain (kinetic) in lbf |
| Pad A | 0.42 | 0.35 | 0.55 | 0.46 | 0.66 | 0.58 |
| Pad B | 0.48 | 0.41 | 0.61 | 0.55 | 0.71 | 0.66 |
| Pad C | 0.45 | 0.38 | 0.56 | 0.47 | 0.75 | 0.64 |
| Comparison Pad D | 0.75 | 0.65 | 0.84 | 0.77 | 0.98 | 0.90 |
| Comparison Pad E | 0.75 | 0.66 | 0.87 | 0.75 | 1.02 | 0.89 |

Figure 3:
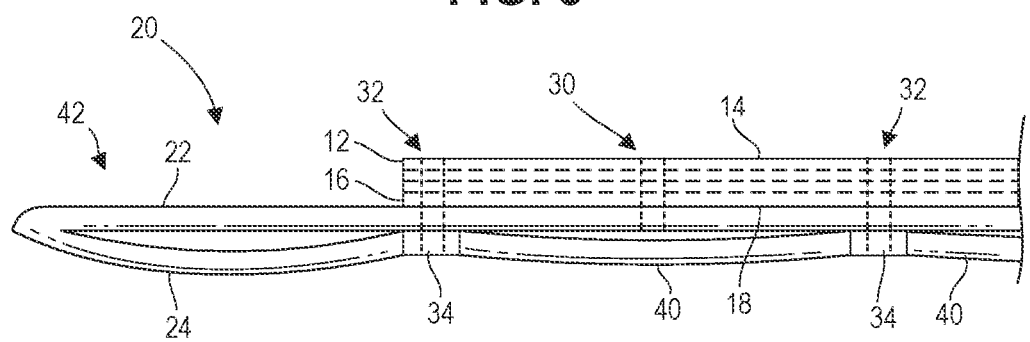
FIG. 3 is an enlarged view of portion 3 of FIG. 1 showing handles formed by the webbing of the absorbent repositioning pad.

Referring to FIGS. 2 and 3, the pad 10 includes webbing 20 to assist in gripping and pulling the pad 10 during repositioning of a patient. The webbing 20 may be secured to the lower layer 16 of the pad 10; for example, at the lower surface 18. The webbing 20 may be a two-layer webbing having longitudinal layers including a first layer 22 secured to the lower surface 18 and a second layer 24 overlapping the first layer 22. The webbing 20 may further including laterally-extending webbing 26 that extends laterally from the longitudinal layers 22, 24.

Regarding the longitudinal layers, as shown in FIG. 3, the first layer 22 of the webbing 20 is secured to the first and second layers 12, 16 of the pad 10, as indicated schematically at 30. For example, the first layer 22 of the webbing 20 may be sewn to the first and second layers 12, 16 of the pad 10 with a chain stitch along the two longitudinal sides of the first layer 22 of the webbing 20 using a heavy filament thread (e.g., Tex 60 or greater).

The second layer 24 of webbing 20 may be secured to the first layer 22 of the webbing 20 and first and second layers 12, 16 of the pad 10, as indicated schematically at 32, at spaced locations 34 of the second layer 24 of the webbing 20. For example, one or more webbing "X" stitches may be sewn at the spaced locations 34 using a thread of Tex 40 or greater. The spaced locations 34 may be spaced approximately 5.5 inches along the second layer 24 of webbing 20 so as to form side handles 40 therebetween.

The first and second layers 22, 24 of the webbing 20 also cooperate to form end handles 42 in bight regions of the webbing. The side handles 40 and end handles 42 provide gripping locations for a caregiver to grip and pull during repositioning of a patient.

Figure 4:
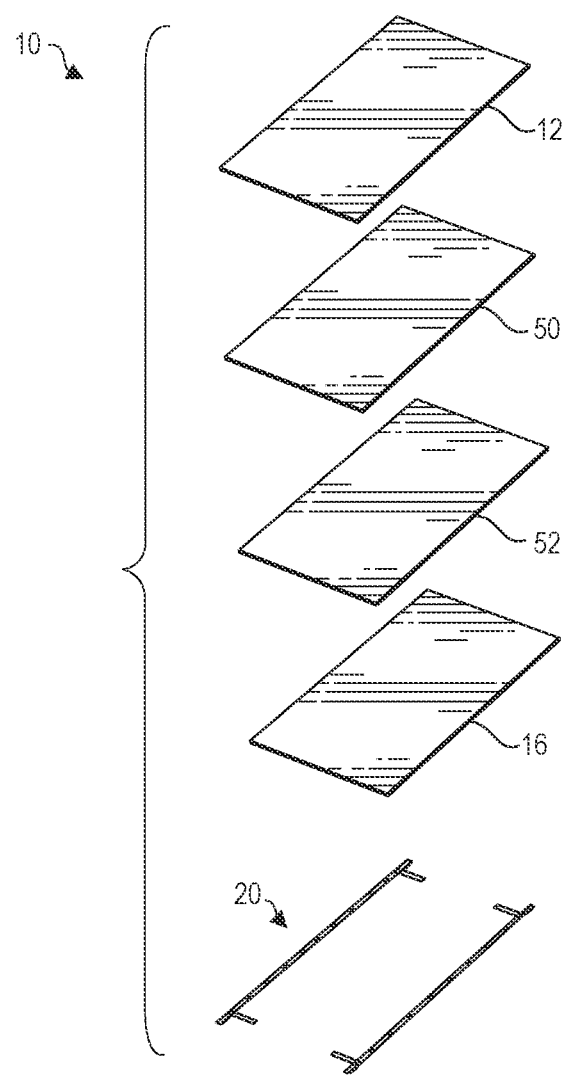
FIG. 4 is an exploded view of the absorbent repositioning pad shown in FIG. 1.
Figure 5:
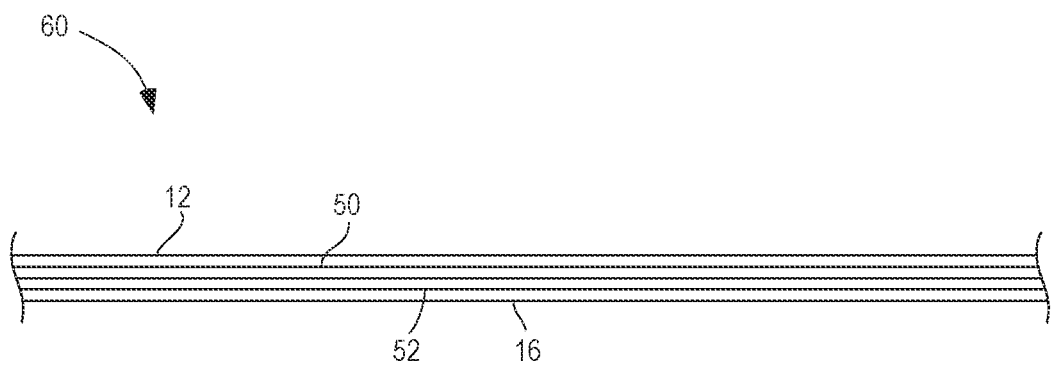
FIG. 5 is an enlarged cross-sectional view of a portion of the absorbent repositioning pad taken along the line 5-5 of FIG. 1 and showing the layers of the absorbent repositioning pad.

Referring to FIGS. 4 and 5, the pad 10 includes one or more intermediate layers disposed between the upper layer 12 and the lower layer 16. As illustrated, the pad 10 includes an upper or first intermediate layer 50 that extends between perimeter edges the upper and lower layers 12, 16, and a lower or second intermediate layer 52 that extends between perimeter edges the upper and lower layers 12, 16 (e.g., between the first intermediate layer 50 and the lower layer 16).

In this way, the upper and lower layers 12, 16 and first and second intermediate layers 50, 52 cooperate to form a pad stack 60 having multiple layers that together form the pad 10. The pad stack 60 includes the upper layer 12, the first intermediate layer 50 disposed below the upper layer 12 (e.g., immediately adjacent the upper layer 12 as shown, or optionally with one or more intermediate layers or components disposed therebetween), the second intermediate layer 52 disposed below the first intermediate layer 50 (e.g., immediately adjacent the first intermediate layer 50 as shown, or optionally with one or more intermediate layers or components disposed therebetween), and the lower layer 16 disposed below the second intermediate layer 52 (e.g., immediately adjacent the second intermediate layer 52 as shown, or optionally with one or more intermediate layers or components disposed therebetween). The pad stack 60 may include fewer than the four layers described herein, or may include additional layers such as adhesive layers or spacer layers.

The first intermediate layer 50 includes an absorbent material, and may be referred to as a "soaker" layer. The first intermediate layer 50 is disposed adjacent to the upper layer 12 to draw moisture through the upper layer 12 and away from a patient disposed thereon. In this way, the first intermediate layer 50 receives and absorbs liquid that passes through the liquid-permeable upper layer 12. The first intermediate layer 50 may include a non-absorbent fiber (e.g., including polyester) and an absorbent fiber (e.g., including rayon). The first intermediate layer 50 of the pad 10 can also or instead comprise a super-absorbent polymer such as polymers and copolymers of acrylic acid and salts thereof (including alkali metal salts such as sodium salts, or alkaline earth salts thereof), polymers and copolymers of methacrylic acid and salts thereof (including alkali metal salts such as sodium salts, or alkaline earth salts thereof), polyacrylamide polymers and copolymers, ethylene maleic anhydride copolymers, cross-linked carboxy-methyl-celluloses, polyacrylate/polyacrylamide copolymers, polyvinyl alcohol copolymers, cross-linked polyethylene oxides, starch grafted copolymers of polyacrylonitrile, etc. The super-absorbent polymers can be cross-linked to suitable degree.

The first intermediate layer 50 absorbs substantially all of the liquid penetrating through from the upper layer 12 when in intended use. In certain embodiments, the first intermediate layer 50 has an absorption capacity in the range of about 50 cc/m$^2$ to about 20,000 cc/m$^2$, for example, about 50 cc/m$^2$, about 100 cc/m$^2$, about 200 cc/m$^2$, about 300 cc/m$^2$, about 400 cc/m$^2$, about 500 cc/m$^2$, about 600 cc/m$^2$, about 700 cc/m2, about 800 cc/m$^2$, about 900 cc/m$^2$, about 1,000 cc/m$^2$, about 1,100 cc/m$^2$, about 1,200 cc/m$^2$, about 1,300 cc/m$^2$, about 1,400 cc/m$^2$, about 1,500 cc/m$^2$, about 1,600 cc/m$^2$, about 1,700 cc/m$^2$, about 1,800 cc/m$^2$, about 1,900 cc/m$^2$, about 2,000 cc/m$^2$, about 3,000 cc/m$^2$, about 4,000 cc/m$^2$, about 5,000 cc/m$^2$, about 6,000 cc/m$^2$, about 7,000 cc/m$^2$, about 8,000 cc/m$^2$, about 9,000 cc/m$^2$, about 10,000 cc/m$^2$, about 11,000 cc/m$^2$, about 12,000 cc/m$^2$, about 13,000 cc/m$^2$, about 14,000 cc/m$^2$, about, 15,000 cc/m$^2$, about 16,000 cc/m$^2$, about 17,000 cc/m$^2$, about, 18,000 cc/m$^2$, about 19,000 cc/m$^2$, or about 20,000 cc/m$^2$, or in each case from that value up to about 20,000 cc/m$^2$, as measured by the ISO 11948-1 test method.

The second intermediate layer 52 may be disposed between the first intermediate layer 50 and the lower layer 16. The second intermediate layer 52 may be sealed to the first intermediate layer 50, for example, via adhesive (e.g., a rubber-based or olefin-based glue) and/or stitching. The adhesive used can be natural or synthetic. Non-limiting examples of such adhesives are hot melt adhesives, drying adhesives, contact adhesives, UV curing adhesives, light curing adhesives, and pressure sensitive adhesives or the like. The second intermediate layer 52 may also be sealed to the lower layer 16. For example, the second intermediate layer 52 may be heat-sealed to the lower layer 16 across the entire (or substantially the entire) second intermediate layer 52, or about a perimeter of the second intermediate layer 52.

The second intermediate layer 52 includes a breathable, liquid-impermeable material such as polyurethane. The second intermediate layer helps block liquid from passing from the first intermediate layer 50 to the lower layer 16, while permitting air to flow from the first intermediate layer 50 to the lower layer 16 and vice versa. For example, the second intermediate layer 52 may include pores that are a 1/20,000 of the size of a liquid droplet, allowing the second intermediate layer 52 to breathe, but small enough to inhibit liquid droplets to pass through. In this way, the pad 10 provides liquid discharge management for incontinent patients while also permitting breathability through the pad.

As discussed, the assembled pad 10 is absorbent to provide incontinence management while having a low-friction lower layer 16 for repositioning a patient. The assembled pad 10 is also a breathable pad. As used herein, the term "breathable" means that the pad 10 is pervious to water vapor and gases. In other words, a "breathable" pad allows water vapor and gases to pass therethrough, but not necessarily liquids. As compared to a vapor-impermeable pad, the breathability of the pad 10 may reduce skin irritations such as rashes when contacting skin for an extended period of time.

Table 2 below shows example breathability, as measured by ASTM E96, of three pads 10 as compared to two alternative pads. Pad A includes a lower surface 18 formed of nylon. Pad B includes a lower surface 18 formed of polyester. Pad C includes a lower surface 18 formed of acetate. Pad D is a Maximum Absorbency Premium Underpad sold by Cardinal Health, and Pad E is a SafetySure MovEase Underpad sold by MTS Medical Supply. As shown, the three pads 10A, B, and C have greater breathability as compared to the two comparison pads D and E.

TABLE 2

|  | g/m$^2$/24 hrs | Conditions | g/m$^2$/24 hrs | Conditions |
|---|---|---|---|---|
| Pad A | 204 | 23 degrees C. | 403 | 32.2 degrees C. |
| Pad B | 163 | 23 degrees C. | 241 | 32.2 degrees C. |
| Pad C | 230 | 23 degrees C. | 383 | 32.2 degrees C. |
| Comparison Pad D | 123 | 23 degrees C. | 145 | 32.2 degrees C. |
| Comparison Pad E | 124 | 23 degrees C. | 139 | 32.2 degrees C. |

As discussed, one or more layers may be secured using one or more adhesives, which may form adhesive layers. The adhesive layer(s) can be continuous, contacting substantially the entire surface area of any two layers adhered together (e.g., at least about 75%, at least about 80%, at least about 85%, at least about 90%, at least about 90%, or about 100% of the surface area of the two layers adhered together, inclusive of all values and subranges therebetween). That is, the adhesive forms an intermediate layer between any two layers adhered together, contacting substantially the entire surfaces between the two layers. Alternatively, the adhesive can be applied in a pattern (e.g., grid) or random fashion whereby the adhesive does not substantially contact the entire surface area of the two layers, but rather forms a discontinuous intermediate layer between the two adhered surfaces. Each of the layers of the pad stack 60 can be adhered together with continuous adhesive layers, or with discontinuous adhesive layers, or some of the adhesive layers can be continuous adhesive layers, and other adhesive layers can be discontinuous layers. Each of the adhesive layers can comprise the same adhesive material, or one or more of the adhesive layers can comprise a different adhesive material. Any suitable glue pattern can be used to connect the layers.

Figure 6:
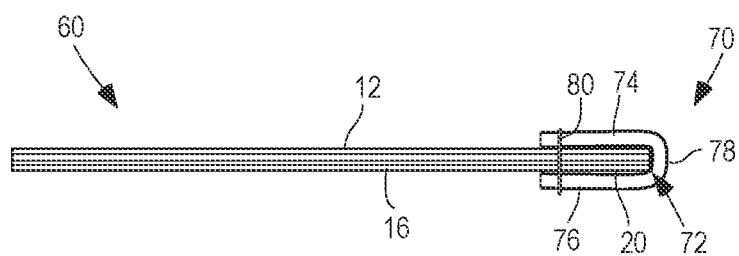
FIG. 6 is an enlarged cross-sectional view of a portion of the absorbent repositioning pad taken along the line 6-6 of FIG. 1 and showing an edge binding of the absorbent repositioning pad.

Referring to FIG. 6, the pad 10 may include an edge binding 70 that extends over one or more edges 72 of the pad 10 to overlap the pad stack 60 and webbing 20. The edge binding 70 includes a first overlap region 74 adjacent the upper layer 12, a second overlap region 76 adjacent the lower layer 16, and an intermediation region 78 that extends between the first and second overlap regions 74, 76. The edge binding 70 may be secured to the pad 10 at the edges 72 (e.g., at the first and second overlap regions 74, 76), as indicated schematically at 80, via one or more stitches, adhesive, or combination thereof.

The edge binding 70 may be formed of the same material as one of the layers of the pad stack 60; for example, the brushed, knit PET of the upper layer 12. The edge binding 70 secures the layers of the pad 10, for example, to prevent unraveling of the layers during washing and use. The edge binding 70 further imparts additional strength to the pad edges 72, which may be prone to exhibit tensile strength failure otherwise.

The materials of the pad stack 60 and webbing 20 of the pad 10 are preferably such that the pad 10 is washable and reusable at least two times. The pad 10 ideally can be laundered in a conventional hospital laundry for at least 25 launderings, and preferably for at least 150 launderings, while still maintaining the ability to absorb patient urine and to function as a repositioning device as described herein.

To assess reusability, sample pads 10 were analyzed prior to any laundering for absorption, acquisition rate and rewet, and operational weight limit parameters. The sample pads included pads having lower surfaces 18 formed of polyester (Pads F), and pads having lower surfaces 18 formed of nylon (Pads G).

The sample pads were then laundered 25 times and subjected to the same testing, with the results shown in Tables 3-5 below. By "laundering" is connoted the following: Eight sample pads were washed in a commercial-grade laundering machine (UniMac UWT045) utilizing a cleaning solution including 2 ounces of alkali, 1.6 ounces of detergent, 2.4 ounces of chlorine, and 0.8 ounces of sour. The wash procedure had a maximum water temperature of 150° F. and a cycle time of 45-minutes. The sample pads were then dried in a commercial-grade drying machine (UniMac UT050NDN0NXA3W0000), set at a 40-minute drying time with a maximum drying temperature of 140° F., and a 3-minute cool down. One cycle of washing and one cycle of drying completes one act of "laundering."

The sample pads were alternated between washing and drying cycles until 25 of both cycles were completed. Prior to and after 25 launders, sample Pads F and G were subjected to absorption testing according to ISO 11948-1. More particularly, each pad was first weighed when dry. The pad was then spread over a drainage screen with the absorbent side down and lowered into a 0.9% NaCl solution test liquid. The pad was then soaked for a total of 30 minutes+/− 30 seconds. The drainage screen was lifted from the test liquid and the pad was allowed to drain for 5 minutes+/−10 seconds. The absorption weight was then calculated by taking the weight of the sample pad when wet and subtracting the weight of the specimen dry. The results of the absorption testing are set forth in Table 3 below, with higher average absorption weight in grams indicative of a higher absorption capacity. As shown, after 25 launders, the average absorption weight in grams of Pads F and G was greater than 3,500 grams.

TABLE 3

|  | Wash Cycles | Avg. Absorption Weight (g) |
| --- | --- | --- |
| Pad F | 0 | 3155.7 |
| Pad F | 25 | 3699.8 |
| Pad G | 0 | 2925.2 |
| Pad G | 25 | 3569.1 |

Prior to and after 25 launders, sample Pads F and G were also subjected to acquisition rate and rewet testing. Prior to washing the pads, ambient conditions when measuring acquisition rate and rewet were 21° C. and 61% relative humidity. After 25 washes, ambient conditions when measuring acquisition rate and rewet were 22° C. and 62% relative humidity.

"Acquisition rate" connotes the following procedure: First, the dry mass of each sample pad was weighed prior to testing. Then, a solution of 500 mL of 0.9% NaCl was applied to each sample pad using a peristaltic pump. The time it took for each sample pad to fully absorb the solution was measured as the rate of acquisition, with a lower time indicating a faster rate of absorption in Table 4 below. As shown, after 25 launders, the average rate of acquisition in seconds of Pads F and G was less than 120 seconds.

"Rewet testing" connotes the following procedure: Once the application was completed, each sample pad sat for 10 minutes. Blotting papers (AATCC blotting papers) were next weighed dry. After the sit time had elapsed, the blotting papers were placed on the sample pad. A mass applying 1.0 psi was placed on top of the blotting paper and was allowed to remain for a 1 minute rewet time. After the rewet time elapsed, the blotting papers were reweighed and their masses were recorded. In Table 4 below, a lower average weight in grams reflects less water re-absorbed onto the blotting paper, which is indicative of a drier upper surface of the sample pad, and thus greater liquid retention of the sample pad. As shown, after 25 launders, the average rewet weight in grams of Pads F and G was approximately 50 grams (+/−5%).

TABLE 4

|  | Wash Cycles | Avg. Rate of Acquisition (sec.) | Avg. Rewet (g) |
| --- | --- | --- | --- |
| Pad F | 0 | 139.04 | 20.26 |
| Pad F | 25 | 119.54 | 50.1 |
| Pad G | 0 | 174.67 | 49.96 |
| Pad G | 25 | 115.31 | 49.17 |

Prior to and after 25 launders, sample Pads F and G were also subjected to operational weight limit testing. A sample pad was attached to a hoist and an initial weight of 300 lb. was applied to an upper surface of the sample pad. Each sample pad was subjected to a given load twenty-five times, or until failure. If the sample pad did not rip after the twenty-five lifts, additional weight was added. When failure occurred, the weight and number of lifts at which the sample pad ripped was recorded. As shown in Table 5 below, Pads F and G had the same average maximum load weight (as indicated by #) prior to laundering. After 25 wash cycles, Pad F supported 80% of the original maximum load weight on average, and Pad G supported 100% of the original maximum load weight on average. The following data represents an average of five samples pre-wash and five samples post-wash, with the percentage of original weight supported defined as the ratio of the average post-wash failure weight to the pre-wash failure weight, expressed as a percentage.

TABLE 5

| | Wash Cycles | Load Weight (lbs.) |
|---|---|---|
| Pad F | 0 | # |
| Pad F | 25 | 80% of # |
| Pad G | 0 | # |
| Pad G | 25 | 100% of # |

Figure 7:
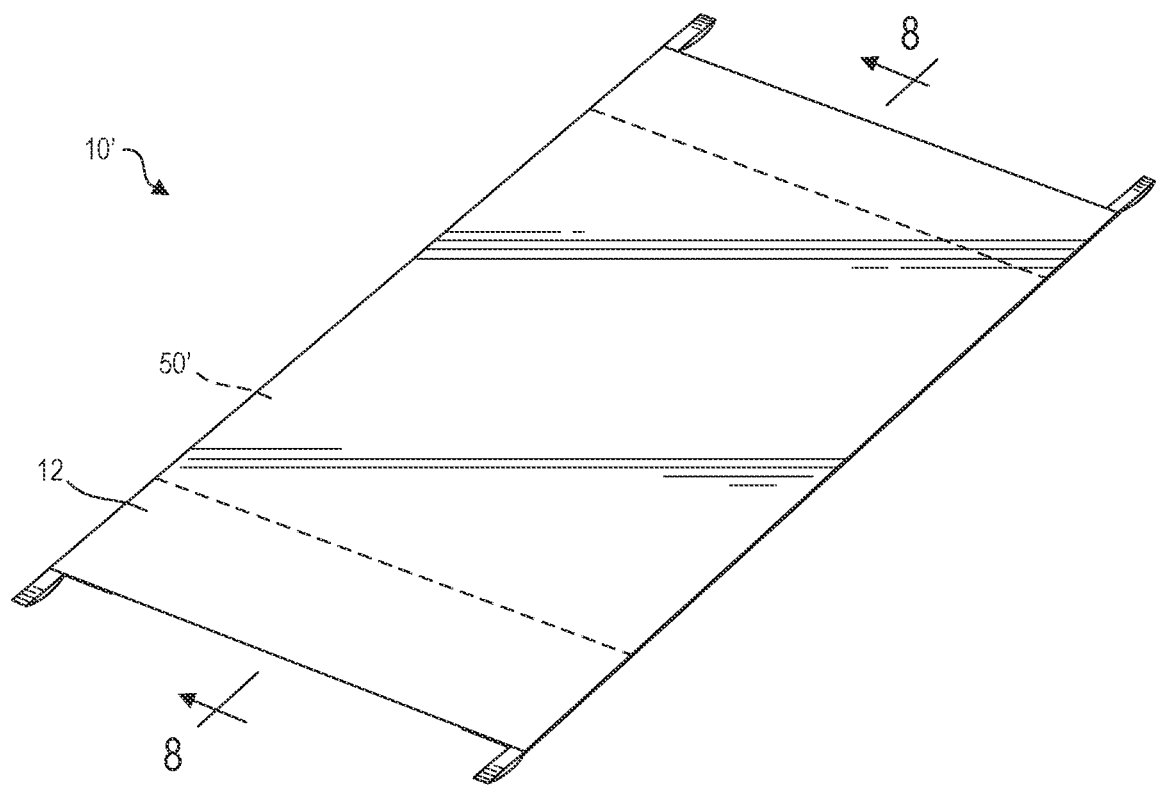
FIG. 7 is a top perspective view of another absorbent repositioning pad having upper and lower layers that extend beyond intermediate layers.
Figure 8:
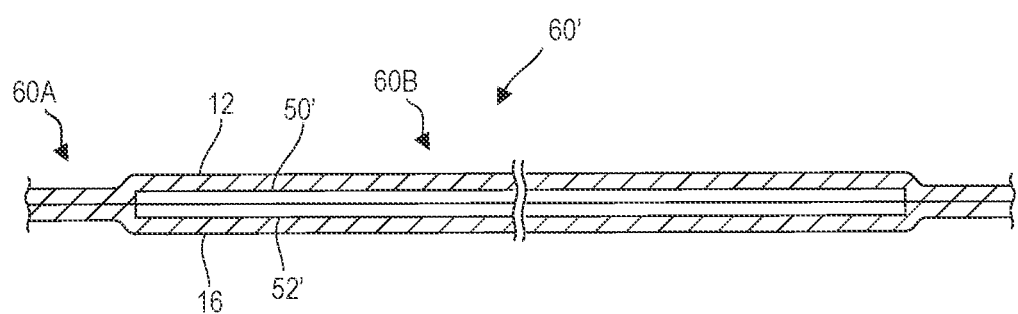
FIG. 8 is an enlarged partial cross-sectional view of a portion of the absorbent repositioning pad taken along the line 8-8 of FIG. 7.

The various layers that form the pad may have generally the same dimensions. For example, referring to FIG. 4, the upper and lower layers 12, 16 may each have a common length (e.g., approximately 53 inches) and a common width (e.g., 34 inches), and the first and second intermediate layers 50, 52 have the same widths and lengths. The dimensions of the intermediate layers may be smaller. Referring to FIGS. 7 and 8, for example, a pad 10' may include first and second intermediate layers 50', 52' that have common widths that are equal to the upper and lower layers 12, 16 (e.g., 34 inches), and may have common lengths that are less than the upper and lower layers 12, 16 (e.g., 36 inches). In this way, as shown in FIG. 8, the pad stack 60' includes a first stack region 60A that includes the upper and lower layers 12, 16, and a second stack region 60B that includes the upper and lower layers 12, 16 and the first and second intermediate layers 50', 52'. The pad 10' may have reduced material costs, for example, as compared to pad 10 of FIGS. 1-5.

When the patient 100 is supported on the absorbent repositioning pad 10, the pad 10 provides incontinence management, as discussed above. The pad 10 also provides for repositioning of the patient 100. For example, with the patient 100 supported on the upper surface 14 of the pad 10, one or more of the side handles 40 and/or end handles 42 may be gripped by a caregiver to slide the low-friction lower surface 18 of the pad 10 across the bed 102 and gurney 104 surfaces to thereby reposition the patient 100.

Figure 9:
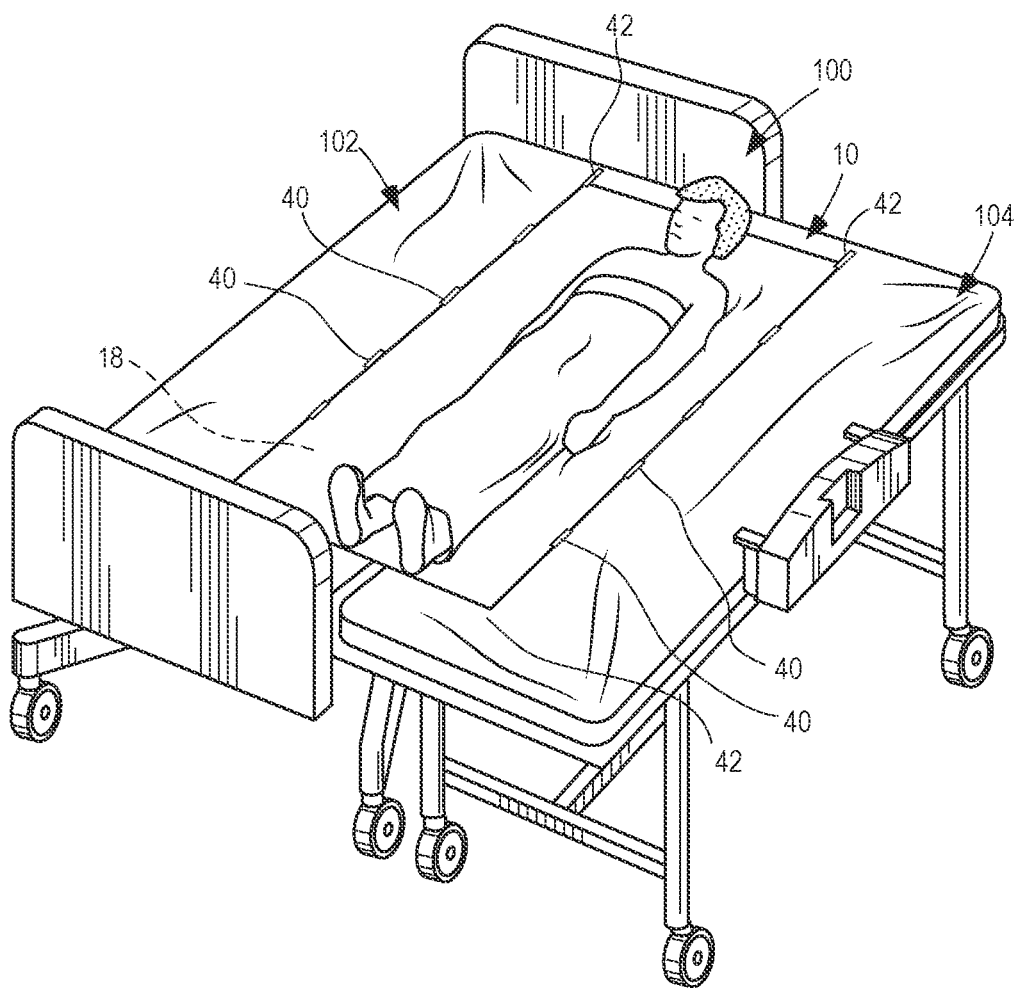
FIG. 9 is a perspective view of a patient being transferred on an absorbent repositioning pad from a bed to a gurney using the absorbent pad of FIG. 1.

Referring to FIG. 9, the absorbent repositioning pad 10 described herein may be used to reposition a person or patient 100 from one patient support surface, such as a bed 102, to another patient support surface, such as a gurney 104, or vice versa.

Figure 10A:
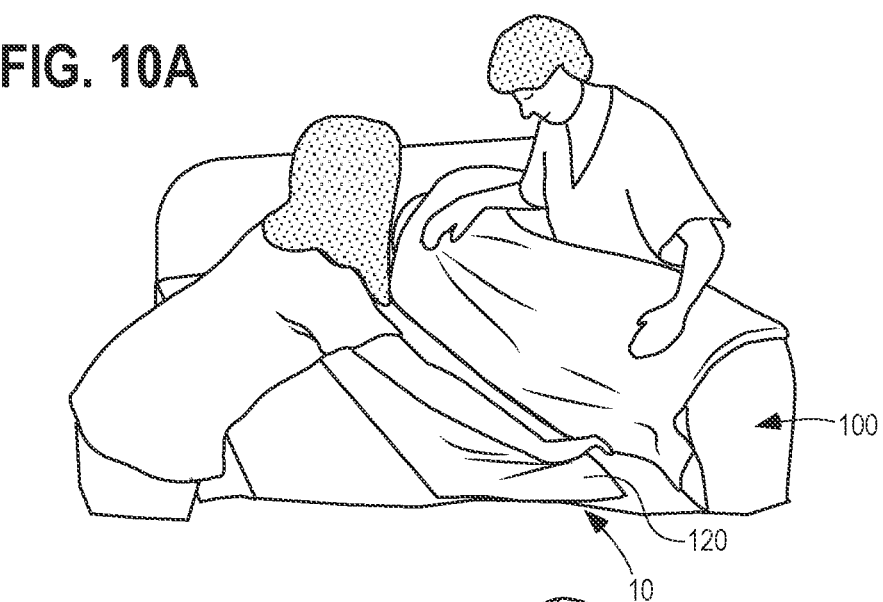
FIG. 10A is a perspective view of a patient being positioned on an absorbent repositioning pad using a patient rolling technique showing the patient in a first lateral decubitus position.
Figure 10B:
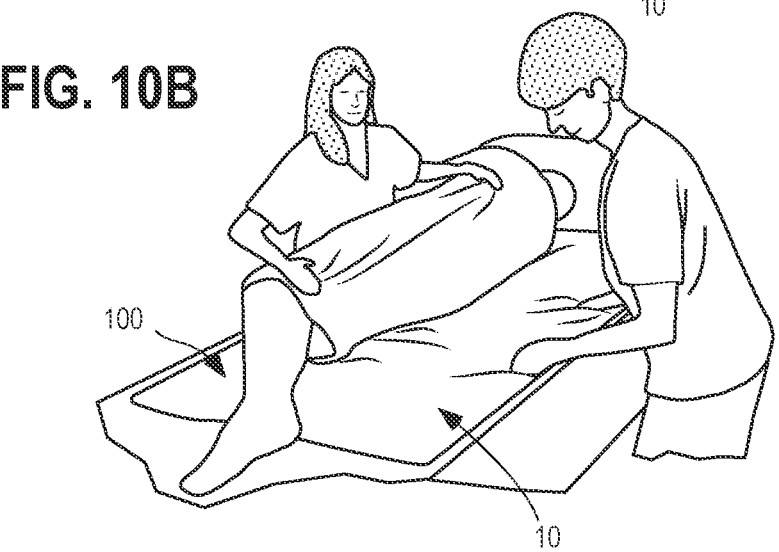
FIG. 10B is a perspective view of the patient rolled over the absorbent repositioning pad from the first lateral decubitus position to a second lateral decubitus position.
Figure 10C:
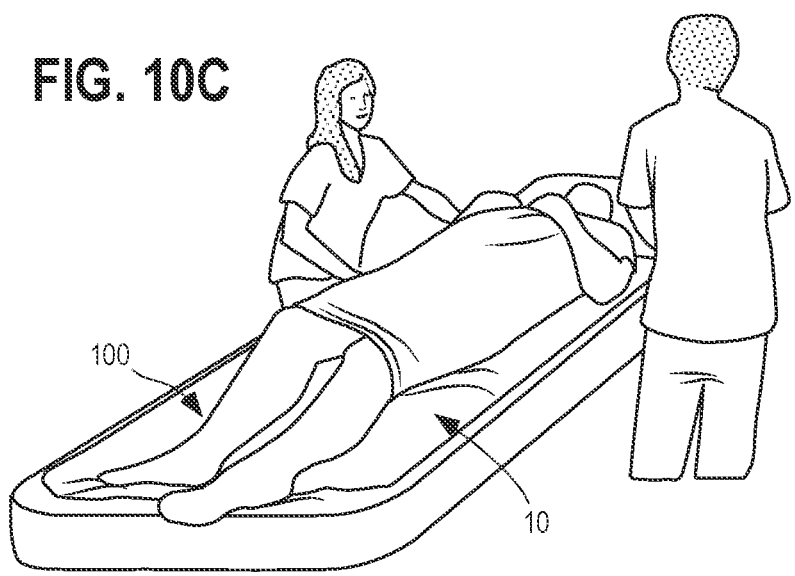
FIG. 10C is a perspective view of the patient rolled over the absorbent repositioning pad from the second lateral decubitus position to a supine position on the absorbent repositioning pad.

Referring to FIGS. 10A-10C, a method of positioning a person or patient 100 on an absorbent repositioning pad can include rolling the person to a first lateral decubitus position shown in FIG. 10A. The method further includes placing the absorbent repositioning pad 10 adjacent the person in the first lateral decubitus position, folding the absorbent repositioning pad 10 to form a folded edge 120, and tucking the folded edge 120 below the person 100 with the person 100 in the first lateral decubitus position. The method further includes rolling the person 100 to a second lateral decubitus position such that the person 100 is above the folded absorbent repositioning pad 10. With the person 100 in the second lateral decubitus position, the method may further include unfolding the absorbent repositioning pad 10 to a planar configuration, as shown in FIG. 10B. The method further includes rolling the person 100 from the second lateral decubitus position to a generally supine position above the absorbent repositioning pad 10, as shown in FIG. 10C. With the person 100 in the generally supine position above the absorbent repositioning pad 10, the pad 10 provides for both incontinence management and subsequent repositioning of the patient 100, as discussed above.

Referring to FIGS. 11A-11C, an alternative system and method for repositioning a patient is shown. The repositioning steps may generally correspond to those described in U.S. Pat. Nos. 8,789,533 and 8,850,634, which are hereby incorporated by reference. As depicted, the patient 100 is placed in an angled resting position by placing two wedges 160 under the patient 100. The method is used with a patient 100 lying on a bed 152 having a bed sheet 154, with the pad 10 laying on top of the bed sheet 154 and the patient 100 resting on the pad 10. In this embodiment, the wedges 160 are positioned under the bed sheet 154 (which may be a fitted sheet), so that the bed sheet 154 is between a ramp surface 162 of a wedge 160 and the pad 10, and a base surface or wall 164 of the wedge 160 is in contact with the mattress 156. In another embodiment, the wedges 160 may be positioned directly under a sheet 158 and over the bed sheet 154, to be in contact with the bottom surface of the sheet 158. It is understood that no bed sheet 154 or other cover for the mattress 156 may be present in some embodiments, in which case the wedges 160 can be placed directly under the sheet 158.

As shown in FIG. 11A, the edge of the bed sheet 154 is lifted, and the wedges 160 are inserted from the side of the bed 152 under the bed sheet 154 and the sheet 158 toward the patient 100. At this point, at least the apex of each wedge 160 may be pushed toward, next to, or at least partially under the patient 100. A low friction material of the wedge 160 can facilitate such insertion. In one embodiment, the wedges 160 should be aligned so that the wedges 160 are spaced apart with one wedge 160 positioned at the upper body of the patient 100 and the other wedge 160 positioned at the lower body of the patient 100, with the patient's sacral area positioned in the space between the wedges 160. It has been shown that positioning the wedges 160 in this arrangement can result in lower pressure in the sacral area, which can reduce the occurrence of pressure ulcers in the patient 100. For example, the wedges 160 may be positioned approximately 10 cm apart.

Once the wedges 160 have been inserted, a caregiver 170 can pull the patient 100 toward the wedge 160 and toward the user 170, such as by gripping the handles 40 on the pad 10, as shown in FIG. 11B. This moves the proximate edges of the pad 10 and sheet 158 toward the back walls 174 of the wedges 160 and toward the user 170, and slides the patient 100 and at least a portion of the sheet 158 up the ramp surface 162, such that the ramp surface 162 partially supports the patient 100 to cause the patient 100 to lay in an angled position. During this pulling motion, low friction materials on the sheet 158 and the wedges 160 provide ease of motion, high friction surface of the wedge 160 resists movement of the wedge 160, and high friction surface of the sheet 158 resists movement of the pad 10 and/or the patient 100 with respect to the sheet 158.

When the patient 100 is to be returned to laying on their back, the wedges 160 can be removed from under the patient 100. The sheet 158 may be pulled in the opposite direction in order to facilitate removal of the wedges 160 and/or position the patient 100 closer to the center of the bed 152. The patient 100 can be turned in the opposite direction by inserting the wedges 160 under the opposite side of the bed sheet 154, from the opposite side of the bed 152, and pulling the sheet 158 in the opposite direction to move the patient 100 up the ramp surfaces 162 of the wedges 160, in the same manner described above.

All methods described herein can be performed in any suitable order unless otherwise indicated herein or otherwise clearly contradicted by context. The use of any examples or exemplary language is intended to be exemplary and not to pose a limitation on the scope of the claims. Any statement herein as to the nature or benefits of the invention or of the preferred embodiments is not intended to be limiting. The claims are intended to cover all modifications and equivalents as permitted by applicable law. Any combination of the above-described elements in all possible variations thereof is encompassed by the invention unless otherwise indicated herein or otherwise clearly contradicted by context. The identification herein of any reference or patent, even if identified as "prior," is not intended to constitute a concession that such reference or patent is available as prior art against the present invention. The identification of any patent is not intended as a concession that the claims of such patent cover any of the heretofore-described embodiments. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A reusable absorbent repositioning pad comprising:
an upper layer including a liquid permeable material;
a lower layer having relatively lower friction surface than the upper layer;
a first intermediate layer between the upper and lower layers and including an absorbent material; and
a second intermediate layer between the first intermediate layer and the lower layer and including a liquid impermeable material,
wherein the pad has an average absorption weight of at least 3,500 grams after 25 launders.

2. The reusable absorbent repositioning pad of claim 1 wherein the upper layer includes a brushed outer surface and the lower layer includes an outer surface that is not brushed.

3. The reusable absorbent repositioning pad of claim 1 wherein the lower layer includes woven extruded fabric.

4. The reusable absorbent repositioning pad of claim 1 wherein at least a portion of the upper layer is hydrophilic.

5. The reusable absorbent repositioning pad of claim 1 wherein the upper layer, lower layer, and first and second intermediate layers include washable materials such that the reusable absorbent repositioning pad is washable and reusable.

6. The reusable absorbent repositioning pad of claim 1 further comprising edge binding that extends about at least a portion of a perimeter of the reusable absorbent repositioning pad.

7. The reusable absorbent repositioning pad of claim 6 wherein the edge binding extends above the upper layer and below the lower layer and is secured to the upper and lower layers.

8. The reusable absorbent repositioning pad of claim 6 wherein the edge binding and the upper layer include the same material.

9. The reusable absorbent repositioning pad of claim 1 wherein the upper layer and the first intermediate layer are liquid-permeable layers for receiving liquid through an upper surface of the upper layer, and wherein the second intermediate layer is a liquid-impermeable layer for maintaining liquid at the first intermediate layer.

10. A reusable absorbent repositioning pad comprising:
an upper layer including a liquid permeable material;
a lower layer having relatively lower friction surface than the upper layer;
a first intermediate layer between the upper and lower layers and including an absorbent material; and
a second intermediate layer between the first intermediate layer and the lower layer and including a liquid impermeable material,
wherein the pad has an average rate of acquisition less than 120 seconds after 25 launders.

11. A reusable absorbent repositioning pad comprising:
an upper layer including a liquid permeable material;
a lower layer having relatively lower friction surface than the upper layer;
a first intermediate layer between the upper and lower layers and including an absorbent material; and
a second intermediate layer between the first intermediate layer and the lower layer and including a liquid impermeable material,
wherein the pad is configured to support at least 80% of an original load weight after 25 launders.

12. A reusable absorbent repositioning pad comprising:
an upper layer including a liquid permeable material;
a lower layer having relatively lower friction surface than the upper layer;
a first intermediate layer between the upper and lower layers and including an absorbent material; and
a second intermediate layer between the first intermediate layer and the lower layer and including a liquid impermeable material,
wherein the pad is configured to support 100% of an original load weight after 25 launders.

13. A method of positioning a person on a reusable absorbent repositioning pad comprising:
rolling the person to a first lateral decubitus position;
placing the absorbent repositioning pad adjacent the person in the first lateral decubitus position, the absorbent repositioning pad including
an upper layer including a liquid permeable material;
a lower layer having relatively lower friction surface than the upper layer;
a first intermediate layer between the upper and lower layers and including an absorbent material; and
a second intermediate layer between the first intermediate layer and the lower layer and including a liquid impermeable material; and
rolling the person to a second lateral decubitus position above the absorbent repositioning pad;
folding the absorbent repositioning pad to form a folded edge; and
tucking the folded edge below the person with the person in the first lateral decubitus position.

14. The method of claim 13 further comprising, with the person in the second lateral decubitus position, unfolding the absorbent repositioning pad.

15. The method of claim 14 further comprising rolling the person from the second lateral decubitus position to a generally supine position above the absorbent repositioning pad.

* * * * *